United States Patent [19]

Doner et al.

[11] Patent Number: 5,068,045

[45] Date of Patent: Nov. 26, 1991

[54] GREASE COMPOSITION CONTAINING ALKOXYLATED AMIDE BORATES

[75] Inventors: John P. Doner, Sewell; Andrew G. Horodysky, Cherry Hill; John A. Keller, Jr., Pitman, all of N.J.

[73] Assignee: Mobil Oil Corporation, Fairfax, Va.

[21] Appl. No.: 596,624

[22] Filed: Oct. 10, 1990

Related U.S. Application Data

[63] Continuation of Ser. No. 511,803, Apr. 17, 1990, abandoned, which is a continuation of Ser. No. 57,155, May 4, 1987, abandoned, which is a continuation of Ser. No. 769,912, Aug. 27, 1985, abandoned.

[51] Int. Cl.$^5$ ............................................. C10M 169/06
[52] U.S. Cl. .............................. 252/32.007 E; 252/41; 252/49.006
[58] Field of Search .................... 252/32.7 E, 41, 49.6

[56] References Cited

U.S. PATENT DOCUMENTS

| | | | |
|---|---|---|---|
| 2,975,134 | 3/1961 | Cook | 252/40.7 |
| 3,361,672 | 1/1968 | Andress et al. | 252/49.6 |
| 3,445,498 | 5/1969 | Cyba | 260/162 |
| 4,374,032 | 2/1983 | Gemmill et al. | 252/49.6 |
| 4,389,322 | 6/1983 | Horodysky | 252/49.6 |
| 4,524,005 | 6/1985 | Horodysky | 252/49.6 |
| 4,529,529 | 7/1985 | Hordoysky | 252/49.6 |

OTHER PUBLICATIONS

Lohuis et al., "The Performance of Fuel Saving Oils", 1980, pp. 261–278.
ASTM Standard Method of Test D2265-67 for "Dropping Point of Lubrication Grease of Wide Temperature Range", 1968, pp. 794–799.

*Primary Examiner*—Jacqueline V. Howard
*Attorney, Agent, or Firm*—Alexander J. McKillop; Charles J. Speciale; Michael J. Mlotkowski

[57] ABSTRACT

The invention is a grease composition comprising a major proportion of a grease, a hydroxy-containing soap thickener and a minor amount of a compound prepared by reacting a boron compound with an alkoxylated amide containing a hydrocarbyl group of 1 to 60 carbon atoms and hydrocarbylene groups of 2 to 6 carbon atoms. Sulfur and/or phosphorous compounds are also incorporated into the composition.

19 Claims, No Drawings

2

GREASE COMPOSITION CONTAINING ALKOXYLATED AMIDE BORATES

This is a continuation of application Ser. No. 511,803, filed on Apr. 17, 1990, which is a continuation of Ser. No. 07/057,155, filed on May 4, 1989 which is a continuation of Ser. No. 06/769,912, filed Aug. 27, 1985, all now abandoned.

BACKGROUND OF THE INVENTION

1. Nature of the Invention

The invention is concerned with grease compositions. More particularly it is concerned with a grease composition comprising oil, hydroxy-containing soap thickener and borated alkoxylated amides and, optionally, phosphorus and sulfur moieties.

2. Prior Art

U.S. Pat. No. 4,389,322 discloses the use of borated adducts of ethoxylated amides as a component of lubricating oils or greases. U.S. Pat. No. 4,389,322 is incorporated herein by reference.

The borated adducts of ethoxylated amides are prepared from ethoxylated compounds having the following generalized structure:

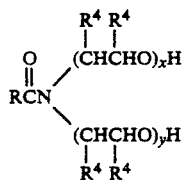

R is a hydrocarbyl group having from about 1 to about 60 (preferably 8 to 30) carbon atoms; R may be alkyl, alkenyl, aralkyl, alkylaryl, etc; x and y may be the same or different and are each a whole number from 0 to about 15, preferably 1 to 5, but the sum of x and y must equal 1 or more, or more preferably, 2 or more. $R^4$ is hydrogen or an alkyl or alkenyl radical of one to six carbon atoms and preferably is hydrogen or a methyl radical.

The borated derivatives can be prepared according to the disclosure in U.S. Pat. No. 4,490,256 which is incorporated herein by reference or by treating the described amides with boric acid optionally in alcoholic solvents such as butanol or pentanol, or optionally hydrocarbon solvents such as benzene, toluene, xylene or mixtures thereof. Reaction temperatures of 70° to 260° C. can be used but 110° to 170° C. is preferred. Reaction times can be 1 to 10 hours or more. Up to a stoichiometric amount or an excess of boric acid can be used to produce a derivative containing 0.05% to 8% or more by weight of boron. Other methods are also available to make similar borated derivatives. For example, the ethoxylated amides may also be borated through transesterification with a trialkyl borate such as tributyl borate (often in the presence of boric acid).

The publication "Manufacture and Application of Lubricating Grease" by C. J. Boner (Reinhold Publishing Company) 1954, pp. 155 and 436, 437 disclose the use of lithium soaps in grease making. The publication "Lubricant Additive" by C. V. Smalheer et al (Leyuis-Hiles Co.) 1967, pp. 1-11, discloses the use of phosphonates and thiophosphonates as additives in lubricants. "Condensed Chemical Dictionary" 9th Edition, (Van Nostrand Reinhold Company) at pages 520 and 938 discloses the use of lithium hydroxystearate in grease making and zinc dialkyldithiophosphate as a lube oil additive.

So far as is known, no effort has been made to employ borated alkoxylated amides in conjunction with a metal hydroxy-containing soap thickener and phosphorous-sulfur compounds. No prior art is known that teaches or suggests the unexpected results obtained by combining the known additives mentioned herein with the particular hydroxy-containing thickener and the borated alkoxylated amides as disclosed herein.

SUMMARY OF THE INVENTION

In accordance with the invention, there is provided an improved grease composition comprising a major proportion of a grease, a hydroxy-containing soap thickener and a minor amount of a compound prepared by reacting a boron compound with a hydroxyl-containing amide of the formula

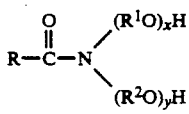

wherein R is a hydrocarbyl group of 1 to 60 carbon atoms, preferably 2 to 50 carbon atoms, and most preferably 8 to 20 carbon atoms, including alkyl, alkenyl, alkoxyl, cycloalkenyl, cycloalkyl, alkaryl, aralkyl, etc. R can also contain oxygen, nitrogen or sulfur atoms.

$R^1$ and $R^2$ are each a hydrocarbylene group or a mixture of hydrocarbylene groups of 2 to 6 carbon atoms;

x is 0 to 15 and y is 0 to 15 provided that x +y equals at least 1. Preferably x+y equals 2 to 10 and more preferably 2 to 6. The boron compound can be a metaborate or similar boron source, including, but not limited to, boric acid, boric oxide or an alkyl borate of the formula

or any similar boron source wherein m is 1 to 3, n is 0 to 2, their sum being 3, and $R^3$ is an alkyl group containing from 1 to 6 carbon atoms. The hydroxy-containing soap thickener used to prepare said grease is present in an amount sufficient to effect an elevation of dropping point and will ordinarily comprise at least 15% by weight of the total thickener composition, the thickener itself making up from 2 to 30 percent of the total grease composition. The increase in dropping point generally can be at least 15° F and can be as great as 200° F. to 250° F. Phosphorus and sulfur compounds can also be added optionally to provide an even higher dropping point. The terms "hydrocarbyl" and "hydroxyhydrocarbyl" include alkyl, aryl, aralkyl, alkaryl and cycloalkyl groups and can also include oxygen or sulfur.

Preferably the hydroxyl-containing amide is overborated. By "overborated" is meant the presence in the borated product of more than a stoichiometric amount of boron up to a 100 to 1000 percent excess.

The hydroxyl-containing amides can be conveniently obtained from commercial sources or prepared in any manner known in the art. For example, the ethoxylated amides can be prepared by the reaction of the appropriate hydrocarbyl amide with ethylene oxide, optionally in the presence of a catalyst, to form the corresponding ethoxylated amide. The ethoxylated amides can also be prepared by the reaction of a hydrocarbyl carboxylic acid with an ethoxylated amine, e.g., bis(2-hydroxyethyl)- oleamide can be formed by the reaction of oleic acid and diethanol amine.

Suitable amides for making the borated product used in this invention include bis(2-hydroxyethyl)oleamide, bis(2-hydroxypropyl)oleamide, 2-hydroxyethyloleamide, 2-hydroxypropyloleamide, polyethoxylated (7) oleamide, polypropoxylated (7) oleamide, each of the above corresponding tallowamides, hydrogenated tallowamides, stearamides, isostearamides, linoleamides, decanoamides, dodecanoamides, cocoamides, naphtenamides, and mixtures of the above and similar amides including, as illustrated, bis(2-hydroxyethyl)-tallowamide, bis(2-hydroxypropyl) hydrogenated tallowamide, 2-hydroxyethyl stearamide, 2-hydroxypropyl isostearamide, polythoxylated (7) linoleamides, polypropoxylated decanoamides, and polythoxylated (5)-polypropoxylated (5) dodecanoamides and all such mixtures of these.

The borated hydroxyl-containing amides used in the composition of this invention can be made by reacting an alkoxylated amide as defined above with a boron compound, such as boric oxide, a metaborate, boric acid which is preferred, an alkyl borate or mixtures thereof. The alkyl borates include the mono-, di- and trialkyl borates, such as the mono-, di- and trimethyl borates, mono-, di- and triethyl borates, mono-, di- and tripropyl borates, mono-, di- and tributyl borates, mono-, di- and tripentyl borates and mono-, di- and trihexyl and tripentyl borates and mono-, di- and trihexyl borates. This reaction is carried out at elevated temperatures of 70° C. to 270° C., optionally in the presence of solvents or catalysts.

A narrow class of thickening agents is used to make the grease of this invention. The thickening agents contain at least a portion of alkali metal, alkaline earth metal or amine soaps of hydroxyl-containing fatty acids, fatty glycerides and fatty esters having from 12 to about 30 carbon atoms per molecule. The metals are typified by sodium, lithium, calcium and barium. Preferred is lithium. Preferred members among these acids and fatty materials are 12-hydroxystearic acid and glycerides containing 12-hydroxystearates, 14-hydroxystearic acid, 16-hydroxystearic acid and 6-hydroxystearic acid, and methyl or related esters of the above hydroxystearic acids, or mixtures thereof.

The entire amount of thickener used in the grease composition need not be derived from the aforementioned members. Significant benefit can be attained using as little thereof as about 5 to 15% by weight of the total thickener and up to 100% of the total thickener. A complementary amount, i.e., up to about 85% by weight of the total thickener of a wide variety of thickening agents can be used in the grease of this invention. Included among the other useful thickening agents are alkali and alkaline earth metal soaps of methyl-12-hydroxystearate, diesters of a $C_4$ to $C_{12}$ dicarboxylic acid and tall oil fatty acids. Other alkali or alkaline earth metal fatty acids containing from 12 to 30 carbon atoms and no free hydroxyl may be used. These include soaps of stearic and oleic acids.

Greases benefiting from the borated additive can be produced by any of the commonly used manufacturing techniques which include open or closed kettle saponification. Saponifications can also be carried out in pressure vessels, commonly known as contactors, at a variety of temperature and pressures. Continuous grease production type equipment can also be used to produce the grease which will be treated with the borated additive. Operating temperatures and pressures are variable as with the conditions normally used to carry out the saponification for the type of reactants involved; but the temperatures generally range from room temperature (25° C.) to 232° C. and pressures as high as 190 psig and as low as vacuum.

Another group of thickening agents comprises substituted ureas, phthalocyanines, indanthrene, pigments such as perylimides, pyromellitdiimides, and ammeline, as well as certain hydrophobic clays. These thickening agents can be prepared from clays which are initially hydrophilic in character, but which have been converted into a hydrophobic condition by the introduction of long-chain hydrocarbon radicals into the surface of the clay particles prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. These methods of grease manufacture, since it is well known to those skilled in the art, is believed to require no further discussion, and does not form a part of the present invention.

The third member(s) that may be present in the grease composition are the phosphorus and sulfur moieties. Both of these can be present in the same molecule, such as in a metal or non-metal phosphorodithioate of the formula

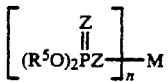

wherein $R^5$ is a hydrocarbyl group containing 3 to 18 carbon atoms. $R^5$ can also contain a hydroxyl or ester radical and can contain additional sulfur. M is preferably a metal, but may be a non-metal, such as one of those mentioned hereinbelow, n is the valence of M and Z is oxygen or sulfur, at least one Z being sulfur. The phosphorodithioate can also be complexed as in a zinc complexed zinc phosphorodithioate.

In this compound, $R^5$ is preferably an alkyl group and may be a propyl, butyl, pentyl, hexyl, octyl, decyl, dodecyl, tetradecyl or octadecyl group, including those derived from isopropanol, propanol, butanol, isobutanol, sec-butanol, 4-methyl-2-pentanol, 2-ethylhexanol, oleyl alcohol, and mixtures thereof. Further included are alkaryl groups such as butylphenyl, octylphenyl, nonylphenyl and dodecylphenyl groups. The phosphorodithioate may also be derived from a diol such as 1,2-decanediol, 1,3-pentanediol and similar $C_4$ to $C_{20}$ diols or can be derived from hydroxyesters.

The metals embraced by M include those in Groups IA, IB, IIA, IIB, VI and VIII of the Periodic Table. Metals that may be mentioned are lithium, sodium, calcium, zinc, cadmium, silver, gold and molybdenum. The Periodic Table of reference here is that published by Fisher Scientific Company designated Cat. No. 5-702-10, Copyright 1978. Non-metallic ions include organic groups derived from vinyl esters such as vinyl acetate, vinyl ethers such as butyl vinyl ether and epoxides such as propylene oxide and 1,2-epoxydodecane.

The non-metallic ions may also be derived from nitrogenous compounds such as those derived from hydrocarbyl amines and diamines, including oleylamine and N-oleyl-1,3-propylenediamine and such as the imidazolines and oxazolines.

The phosphorus and sulfur moieties can also be supplied from the combination of two separate compounds, such as the combination of (1) a dihydrocarbyl phosphite having 2 to 10 carbon atoms in each hydrocarbyl group or mixtures of phosphites and (2) a sulfide such as sulfurized isobutylene, dibenzyl disulfide, sulfurized terpenes, phosphorodithionyl disulfide and sulfurized jojoba oil. The phosphites include the dibutyl, dihexyl, dioctyl, didecyl and similar phosphites. Phosphate esters containing 4 to 20 carbon atoms in each hydrocarbyl group, such as tributyl phosphate, tridecyl phosphate, tricresyl phosphate and mixtures of such phosphates, can also be used. The phosphorus and sulfur can also be supplied by a single compound such as phosphorodithionyl disulfide, and related phosphorus and/or sulfur compounds or mixtures of any of the above.

In summary, it is essential to the practice of this invention, in which greases having improved dropping points are obtained, that at least the borated alkoxylated amides and the hydroxy-containing thickener be included in the grease composition. Thus:

first, with respect to the preparation of the grease, the thickener will have at least about 15% by weight of a metal or non-metal hydroxyl-containing soap therein, the total thickener being preferably from about 3 percent to about 20 percent by weight of the grease composition;

second, there will be added to the grease from about 0.1 percent to about 10 percent by weight, preferably about 0.5 percent to about 2.0 percent of a borated alkoxylated amide or mixture of amides, in which such alkoxylated amide has been reacted with at least 5 stoichiometric percent and more preferably at least an equimolar amount of boron compound or an excess; and as a third component optionally, the composition may have therein from 0.5 percent to about 10 percent by weight, preferably from 1 percent to 2 percent by weight, of phosphorus- and sulfur-containing compounds or a mixture of two or more compounds which separately supply the phosphorus and sulfur moieties. If separate compounds are used, an amount of the mixture equivalent to the above concentration levels is used to supply desired amounts of phosphorus and sulfur.

It is noted that, when the hydroxy-containing thickener is used with the borated alkoxylated amide, the dropping point of the grease is consistently unexpectedly higher than with a grease from the same grease vehicle and the same borated compound, but with a different thickener, e.g., a non-hydroxy-containing thickener. Thus, the broad invention is to a grease composition containing the borated alkoxylated amide and the hydroxy-containing thickener. Phosphorus and sulfur moieties can be additionally included to provide further substantial improvements in the dropping point.

In general, the reaction products of the present invention may be employed in any amount which is effective for imparting the desired degree of high temperature stability.

The greases of the present invention can be made from either a mineral oil or a synthetic oil, or mixtures thereof. In general, mineral oils, both paraffinic, naphthenic and mixtures thereof, may be of any suitable lubricating viscosity range, as for example, from about 45 SSU at 38° C. (100° F.) to about 6000 SSU at 38° C., and preferably from about 50 to about 250 SSU at 99° C. (210° F.). These oils may have viscosity indexes ranging to about 100 or higher. Viscosity indexes from about 70 to about 95 are preferred. The average molecular weights of these oils may range from about 250 to about 800. In making the grease, the lubricating oil from which it is prepared is generally employed in an amount sufficient to balance the total grease composition, after accounting for the desired quantity of the thickening agent, and other additive components to be included in the grease formulation.

Base oils used in the grease are mineral, synthetics, other hydrocarbon liquids or mixtures of these. In addition, oxygen-containing fluids can be used such as dibasic acid esters, polyol esters, polyglycols, or phosphate esters. The alkyl benzene-type lubricants are also included. Other fluids that may be used are halogenated fluids, silicones, silicate esters, or polyphenyl ethers. These lubricant fluids can be mixed or used alone as the base oil portion of the grease. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers.

The metallic soap grease compositions containing one or more of the borated hydroxyl-containing amides and hydroxy-containing soap thickeners and, optionally, one or more of the sulfur and phosphorus combinations described herein provide advantages in increased dropping point, improved grease consistency properties, antirust characteristics and potential antifatigue, antiwear and antioxidant benefits unavailable in any of the prior greases known to us. The grease of this invention is unique in that it can be preferably manufactured by the admixture of additive quantities of the borated akoxylated amides to the fully formed soap grease after completion of saponification.

The following Examples will present illustrations of the invention. They are illustrative only, and are not meant to limit the invention.

EXAMPLE 1

Fully Formulated Lithium Hydroxystearate Grease

This example illustrates the dropping point resulting when a grease contains a hydroxy-bearing thickener and a phosphorus sulfur compound, but is absent the borated hydroxyl-containing amide. A lithium hydroxystearate grease thickener was prepared by a saponifying mixture containing 50 weight percent of 12-hydroxystearic acid and the glyceride thereof with lithium hydroxide in a mineral oil vehicle at about 177° C. in a closed contactor. After depressuring and dehydrating the thickener in an open kettle sufficient mineral oil was added to reduce the thickener content to about 9.0%. After the grease had cooled to 99° C., a typical grease additive package, consisting of an amine antioxidant, phenolic antioxidant, metallic dithiophosphate (phosphorodithioate), sulfur-containing metal deactivator and nitrogen containing antitrust additives, was added.

This produced a fully formulated hydroxyl-containing soap grease. The dropping point of this formulated grease was 202° C. (395° F.).

EXAMPLE 2

Lithium Hydroxystearate Base Grease

This example illustrates the dropping point resulting from a grease absent the additive package and borated hydroxyl-containing amide of Example 3. A lithium hydroxystearate-thickened base grease was prepared as generally described for Example 1. No additive package was used in the grease. After reduction of the thickener content to about 10%, the grease (without additives) was cooled and held for subsequent testing. The dropping point of this base grease was 202° C. (395° F.).

EXAMPLE 3

Preparation of Borated bis(2-Hydroxyethyl)oleamide

This example illustrates preparation of the borated hydroxyl-containing amide. A sample of 1800 grams of bis(2-hydroxyethyl)oleamide (obtained commercially as Ethomid 0/12 from Armak Chemical Co.), 200 grams toluene and 266 grams boric acid were placed in a reactor equipped with heater, agitator, and Dean-Stark tube with condenser and refluxed for approximately 7½ hours until all water found in the reaction azeotroped over (maximum temperature was approximately 175°–180° C.). The solvents were removed by vacuum distillation at approximately 180° C. and the product was filtered to form a dark, orange colored viscous liquid.

EXAMPLE 4

This example illustrates preparation of one embodiment of the grease composition of this invention. Two percent of the borated hydroxyl-containing amide of Example 3 was blended into the lithium hydroxystearate thickened base grease of Example 2 at about 260°–280° F.

EXAMPLE 5

This example illustrates the preparation of a second embodiment of the grease composition of this invention containing sulfur and phosphorus compounds. Two percent of the borated alkoxylated amide of Example 3 and 1.5% of zinc dialkyl dithiophosphate were blended into the lithium hydroxystearate thickened base grease of Example 2.

EXAMPLE 6

Lithium Stearate/Palmitate Thickened Base Grease

This example illustrates the dropping point achieved with a grease absent a hydroxy-containing thickener and a borated hydroxyl-containing amide. A lithium stearate/palmitate (50% stearate, 50% palmitate) base grease, not containing any hydroxyl-bearing groups in the soap thickener was prepared for evaluation as generally described in Example 2. The total thickener content was about 10%. The dropping point of the resultant grease was 404° F.

EXAMPLE 7

Two percent of the borated hydroxyl-containing amide of Example 3 was blended into the lithium stearate/palmitate thickened (non-hydroxyl-containing) base grease of Example 6. This example illustrates the dropping point achieved when a non-hydroxyl-containing base grease has added to it a borate material. No improvement in dropping point is observed.

The results, obtained testing the formulated greases with the ASTM D-2265-78 Test, are summarized in Table I.

TABLE I

| | | Dropping Point, ASTM D2265 |
|---|---|---|
| Example 1 | Fully formulated lithium hydroxystearate thickened grease containing no added borated hydroxyl-containing amide | 202° C. (395° F.) |
| Example 2 | Lithium hydroxystearate base grease containing no added borated hydroxyl-containing amides | 202° C. (395° F.) |
| Example 4 | 2% of Borated hydroxyl-containing amide of Example 3 blended into Example 2 base grease | 253° C. (491° F.) |
| Example 5 | 2% of Example 3 and 1.5% zinc dialkyl dithiophosphate blended into Example 2 base grease | 307° C. (584° F.) |
| Example 6 | Lithium stearate/palmitate (50:50) thickened base grease | 207° C. (404° F.) |
| Example 7 | 2% of borated hydroxyl-containing amide of Example 3 blended into Example 6 base grease | 201° C. (393° F.) |

Examples 4 and 5 clearly demonstrate the improved dropping point resulting from the invention. Example 4 shows a 24 percent increase in dropping point through use of the borated ethoxylated amide compound. Example 5 shows a 47 percent increase when both the borated hydroxyl-containing amide and a sulfur phosphorus compound are used with the hydroxy containing thickener.

We claim:

1. An improved grease composition comprising a major portion of a lubricating component and:
   (a) a means for elevating the dropping point of a grease comprising a compound prepared by reacting a boron compound with a hydroxyl-containing amide and
   (b) a hydroxy-containing soap thickener.

2. The composition of claim 1 wherein the hydroxyl-containing amide has the structural formula:

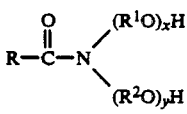

wherein R is a hydrocarbyl group of 1 to 60 carbon atoms and can additionally contain sulfur, oxygen and/or nitrogen;

$R^1$ and $R^2$ are each a hydrocarbylene group or a mixture of hydrocarbylene groups of 2 to 6 carbon atoms;

x is 0 to 15, and y is 0 to 15, provided that x+y equals at least 1.

3. The composition of claim 2 wherein R contains sulfur, oxygen or nitrogen atoms.

4. The composition of claim 2 wherein said borated hydroxyl-containing amide is present in said grease composition in an amount of between 0.2 and about 10 percent by weight.

5. The composition of claim 2 wherein the total amount of thickener added is between about 3 and about 20 percent by weight of the total composition.

6. The composition of claim 5 wherein the thickener contains at least 15 percent by weight of hydroxy-containing thickener.

7. The composition of claim 2 wherein said grease contains additionally between about 0.2 and about 10 percent by weight of phosphorus and sulfur containing compounds.

8. The composition of claim 2 wherein the hydroxyl-containing amide is selected from the group consisting of bis(2-hydroxyethyl)oleamide, bis(2-hydroxypropyl)oleamide, 2-hydroxyethyloleamide, 2-hydroxypropyloleamide, polyethoxylated (7) oleamide, polypropoxylated (7) oleamide, each of the above corresponding tallowamides, hydrogenated tallowamides, stearamides, isostearamides, linoleamide, decanoamides, dodecanoamides, naphthenamides, and mixtures of the above and bis(2-hydroxyethyl)tallowamide, bis(2-hydroxypropyl) hydrogenated tallowamide, 2-hydroxyethyl stearamide, 2-hydroxypropyl isostearamide, polythoxylated (7) linoleamides, polypropoxylated decanoamides, and polythoxylated (5)-polypropoxylated (5) dodecanoamides.

9. The composition of claim 7 wherein said hydroxy-containing carboxylate thickener is lithium hydroxystearate.

10. The composition of claim 7 wherein said phosphorus and sulfur compound is zinc dihydrocarbyldithiophosphate.

11. The composition of claim 2 wherein the lubricating component is mineral oil, synthetic oil, or a mixture thereof.

12. The composition of claim 11 wherein the synthetic oils are polyglycols, synthetic hydrocarbons, alkyl benzenes, dibasic acid esters, polyol esters, phosphate esters or mixtures thereof.

13. The composition of claim 2 wherein the boron compound is selected from the group consisting of a metaborate, boric acid, boric oxide, or an alkyl borate of the formula $(R^3O)_m B(OH)_n$ wherein m is 1 to 3, n is 0 to 2, the sum of m and n being 3 and $R^3$ is an alkyl group containing from 1 to 6 carbon atoms.

14. A method for elevating the dropping point of a grease composition comprising incorporating into said grease (1) means for elevating the dropping point of a grease comprising a borated hydroxyl-containing amide resulting from a reaction of a boron compound with a hydroxy-containing amide and (2) a hydroxy-containing or polyhydroxy-containing soap thickener.

15. The method of claim 14 further comprising the step of adding to said grease composition one or more compounds containing sulfur and phosphorus.

16. The method of claim 15 wherein said phosphorus and sulfur containing compound is zinc dihydrocarbyldithiophosphate.

17. The method of claim 14 wherein the hydroxy-containing soap thickener is at least 15% by weight of the total thickener in said grease composition.

18. A method for making grease wherein a liquid lubricant is mixed with a thickening agent, the improvement comprising adding to said grease (a) means for elevating the dropping point of a grease comprising a borated hydroxyl-containing amide and (b) a hydroxy-containing thickener.

19. The method of claim 18 further comprising the step of adding one or more compounds containing sulfur and phosphorus.

* * * * *